(12) United States Patent
Puhalla et al.

(10) Patent No.: US 11,071,245 B2
(45) Date of Patent: Jul. 27, 2021

(54) SEEDING MACHINE INCLUDING VARIABLE FORCE TRENCH CLOSER

(71) Applicant: Deere & Company, Moline, IL (US)

(72) Inventors: Jeffery S. Puhalla, Hawley, MN (US); Travis J. Davis, Polk City, IA (US)

(73) Assignee: DEERE & COMPANY, Moline, IL (US)

( * ) Notice: Subject to any disclaimer, the term of this patent is extended or adjusted under 35 U.S.C. 154(b) by 173 days.

(21) Appl. No.: 16/394,676

(22) Filed: Apr. 25, 2019

(65) Prior Publication Data
US 2020/0337218 A1 Oct. 29, 2020

(51) Int. Cl.
| | |
|---|---|
| A01C 5/06 | (2006.01) |
| A01B 63/32 | (2006.01) |
| G01N 9/00 | (2006.01) |
| G01N 33/24 | (2006.01) |
| G01S 13/08 | (2006.01) |
| A01C 7/20 | (2006.01) |

(52) U.S. Cl.
CPC .............. *A01C 5/068* (2013.01); *A01B 63/32* (2013.01); *A01C 7/203* (2013.01); *A01C 7/205* (2013.01); *G01N 9/00* (2013.01); *G01N 33/24* (2013.01); *G01S 13/08* (2013.01); *G01N 2033/245* (2013.01)

(58) Field of Classification Search
CPC ......... A01C 5/066; A01C 5/068; A01B 63/32; G01N 9/00; G01N 33/24; G01N 2033/245; G01S 13/08
See application file for complete search history.

(56) References Cited

U.S. PATENT DOCUMENTS

| | | | |
|---|---|---|---|
| 5,936,234 A | 8/1999 | Thomas et al. | |
| 7,938,074 B2 | 5/2011 | Liu | |
| 8,910,582 B2 | 12/2014 | Mariman et al. | |
| 10,838,432 B2 * | 11/2020 | Barrick | ............... A01B 79/005 |

(Continued)

FOREIGN PATENT DOCUMENTS

| | | |
|---|---|---|
| WO | WO 2016/182906 A1 | 11/2016 |
| WO | WO 2017/197292 A1 | 11/2017 |

OTHER PUBLICATIONS

European Search Report issued in EP Application No. 20171616.4-1011 dated Sep. 16, 2020 (8 pages).

*Primary Examiner* — Thomas B Will
*Assistant Examiner* — Ian A Normile
(74) *Attorney, Agent, or Firm* — Brinks Gilson & Lione

(57) ABSTRACT

An agricultural seeding machine includes a trench closer assembly and a sensing device configured to sense an aspect of the soil without contacting the soil and to output a sensed signal corresponding to the aspect of the soil. A processing device processes the sensed signal to generate a processed sensed signal, and compares a characteristic of the processed sensed signal to a stored signal characteristic representative of a soil condition. A trench closure quality metric is determined and provided via a user interface. Additionally, in response to and based upon the comparison, the processing device may automatically adjust the force applied to the soil by the soil contacting member. In this manner, the seeding machine utilizes a feedback signal to determine how well a trench is closed and can adjust the performance of the trench closer assembly in accordance with that feedback.

20 Claims, 6 Drawing Sheets

(56) References Cited

U.S. PATENT DOCUMENTS

| | | |
|---|---|---|
| 2012/0255475 A1 | 10/2012 | Mariman et al. |
| 2015/0012189 A1 | 1/2015 | Henry et al. |
| 2018/0128933 A1 | 5/2018 | Koch et al. |
| 2018/0224537 A1 | 8/2018 | Taylor et al. |
| 2018/0242517 A1* | 8/2018 | Davis ..................... G01S 19/42 |
| 2019/0059206 A1* | 2/2019 | Stanhope ............. A01B 63/008 |

* cited by examiner

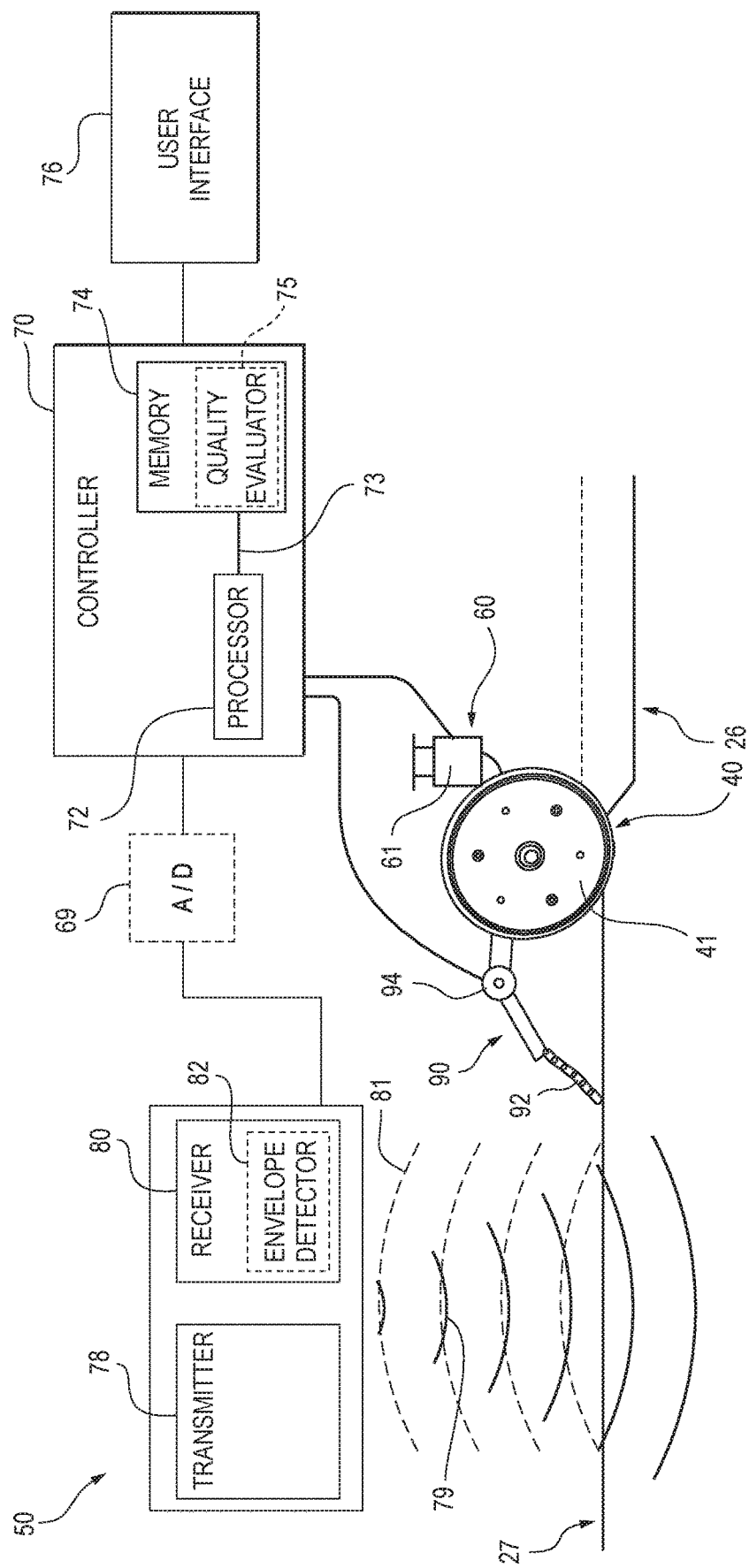

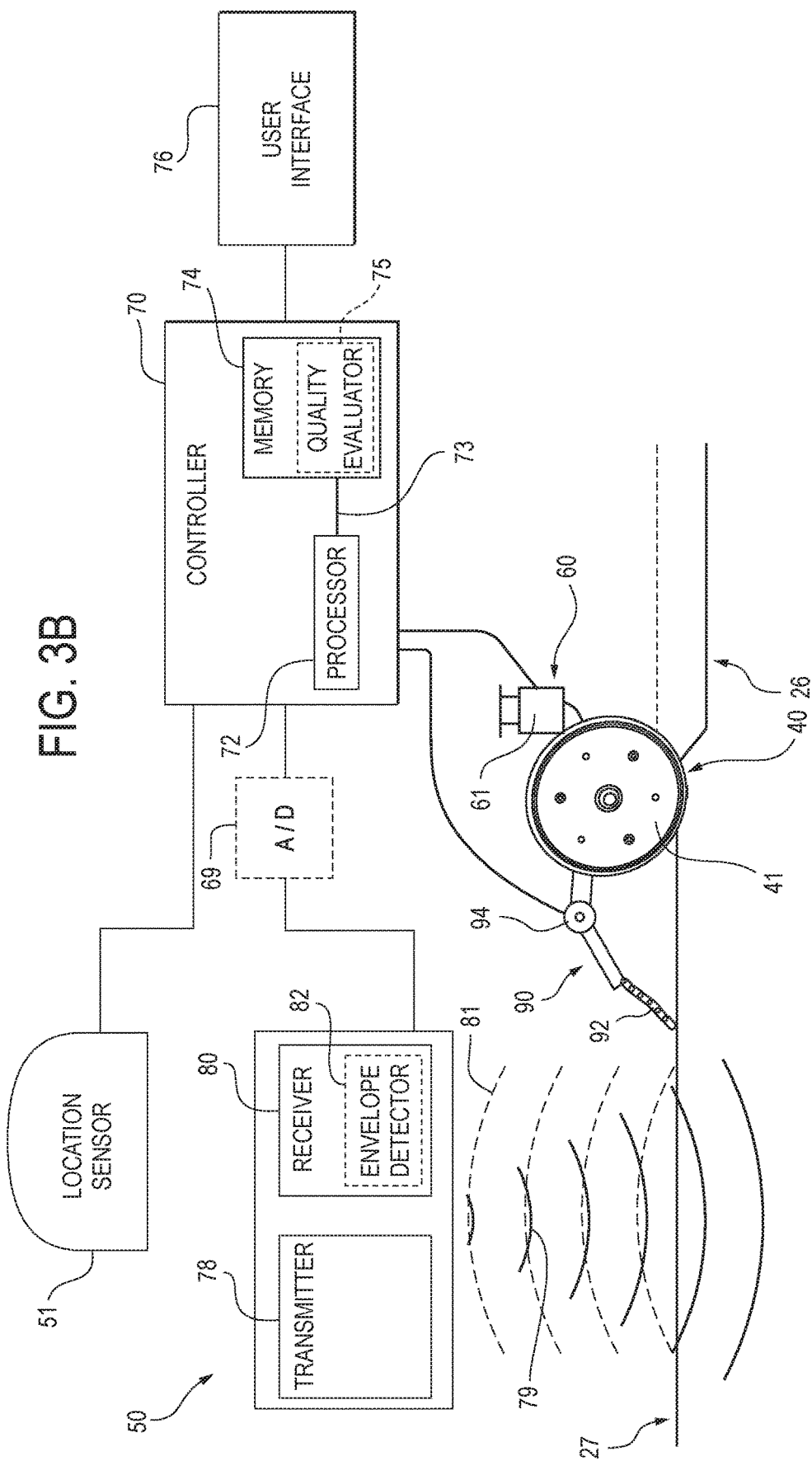

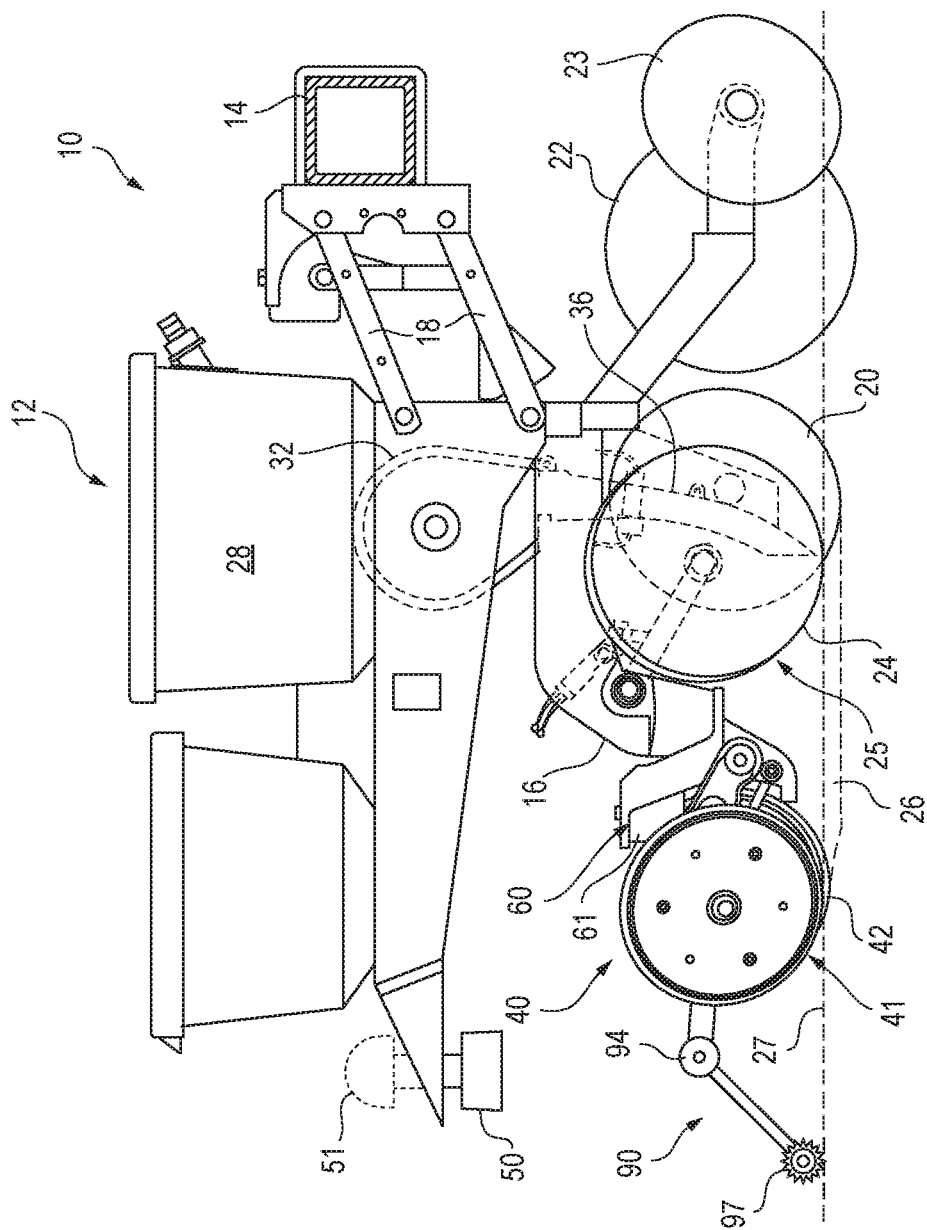

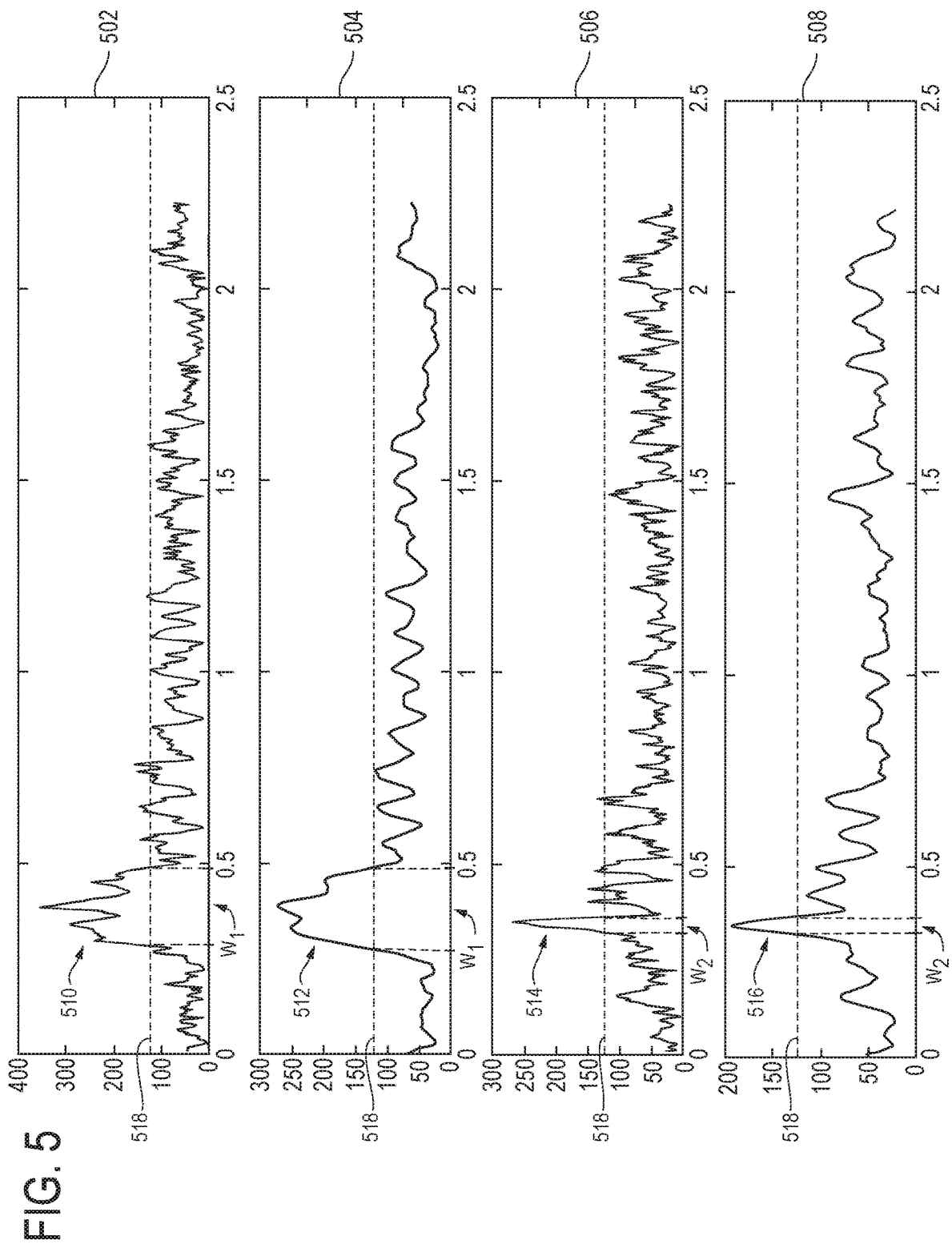

SEEDING MACHINE INCLUDING VARIABLE FORCE TRENCH CLOSER

TECHNICAL FIELD

This disclosure relates to sensing devices and systems for closing trenches by a seeding machine.

BACKGROUND

Seeding machines typically employ a plurality of planting rows, each planting row including a trench opener, a seed dispenser, and a trench closing assembly. Proper and complete closure of the trench is essential to provide good seed-to-soil contact and to provide an ideal and/or uniform seed depth. These factors help the seed to germinate properly and the resulting plant to have a healthy start, thereby reducing crop loss or failure of the seeds to germinate (e.g., by leaving seeds uncovered or within air pockets). Further, controlling these factors helps control the timing of when the plants within a field will sprout and come up out of the ground, thereby providing a fairly uniform behavior of the crops to allow for optimal treatment of the entire field during the growing season. This helps produce optimal crop yield.

SUMMARY

In various embodiments, an agricultural seeding machine includes a trench closer assembly further including a soil contacting member. The trench closer assembly is configured to vary a force applied to the soil by the soil contacting member. The agricultural seeding machine also includes a sensing device configured to sense at least one aspect of the soil without contacting the soil, and output a sensed signal corresponding to the at least one aspect of the soil. Additionally, the agricultural seeding machine also includes a processing device coupled to the sensing device and the trench closer assembly. The processing device is configured to receive the sensed signal from the sensing device, process the sensed signal to generate a processed sensed signal, and compare a characteristic of the processed sensed signal to at least one stored signal characteristic representative of at least one soil condition. In response to and based upon the comparison, a user interface provides an indication of a metric representative of a quality of the trench closing to a user. In certain embodiments, the processing device automatically adjusts the force applied to the soil by the soil contacting member of the trench closer assembly based on the comparison. In this manner, the seeding machine acquires and utilizes a feedback signal to determine how well a planting trench is being closed and can adjust the performance of the trench closer assembly in accordance with that feedback. This can provide for optimal trench closing, thereby improving seed-to-soil contact and managing seed depth to ultimately improve yield.

BRIEF DESCRIPTION OF THE DRAWINGS

FIG. 3A shows an example schematic diagram of a portion of the agricultural seeding machine according to various embodiments.

FIG. 3B shows another example schematic diagram of a portion of the agricultural seeding machine according to various embodiments.

FIG. 4 shows another example planting row unit of an agricultural seeding machine utilizing an alternative secondary closer member according to various embodiments.

FIG. 5 shows example graphs of sensed signals according to various embodiments.

DETAILED DESCRIPTION

Figure 1:
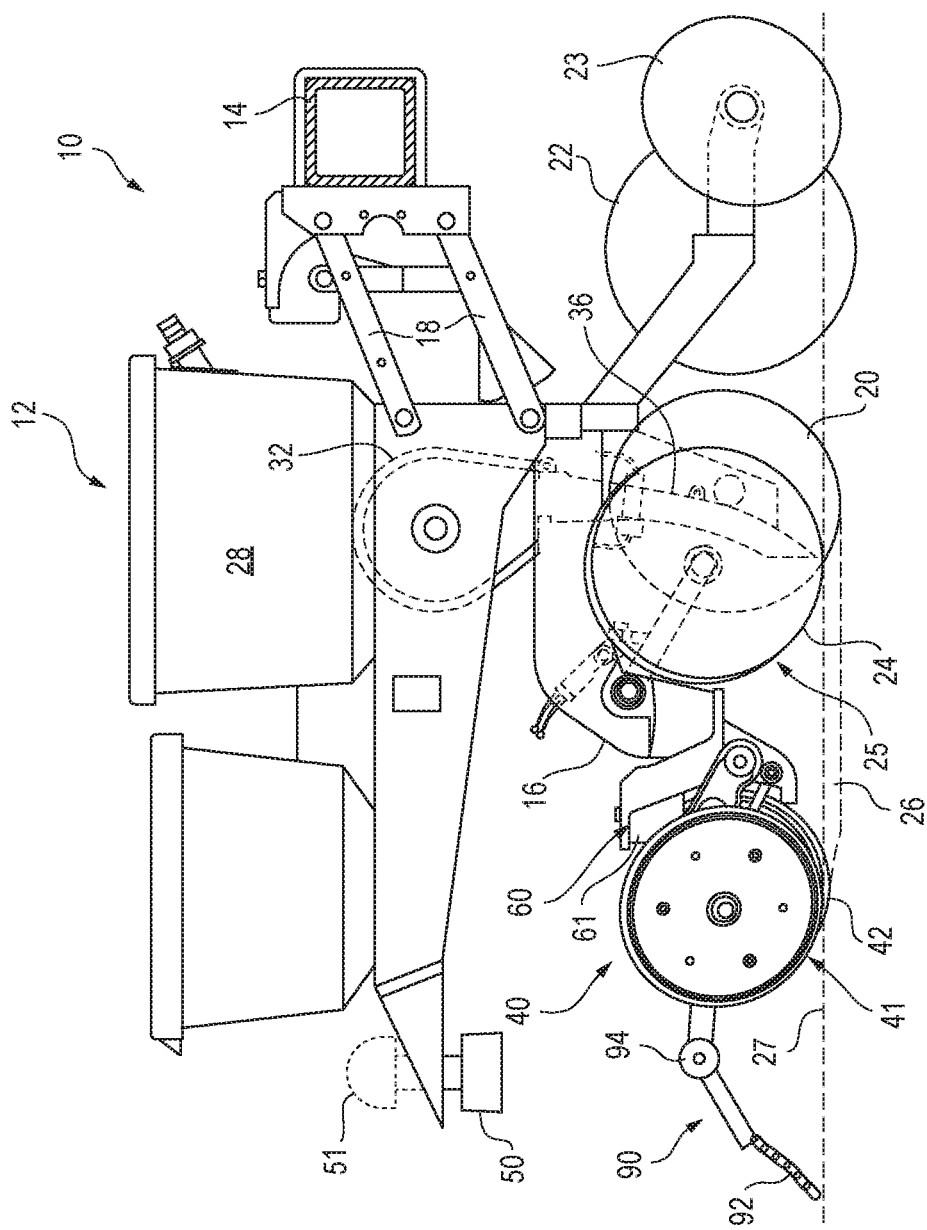
FIG. 1 shows an example planting row unit of an agricultural seeding machine according to various embodiments.

With reference to the figures, FIG. 1 shows an example row planting unit 12 of an agricultural seeding machine 10 according to various embodiments. As shown, seeding machine 10 is in the form of a row crop planter but may also be other forms of machines. FIG. 1 illustrates a single row planting unit 12 of a multi-row planter. In certain implementations, each row planting unit 12 of a multi-row planter may be substantially identical and connected to a machine frame 14 shown as a tool bar. Only a single row planting unit 12 is shown and described below in FIG. 1 for sake of simplicity. Row planting unit 12 may include a multi-part row unit frame 16 that may be attached to the tool bar by a parallel linkage 18. The tool bar is coupled to a traction unit (not shown), such as an agricultural tractor. For example, tool bar may be coupled to an agricultural tractor using a draw bar or 3-point hitch assembly. The tool bar may be coupled with transport wheel assemblies, marker arms, or other assemblies, which may be of conventional design and not shown for clarity.

In various embodiments, the frame 16 carries a double disc trench opener 20 for forming a seed trench 26 in soil 27. An optional coulter wheel 22 and row cleaner 23, particularly for use in no till situations, may be placed ahead of double disc trench opener 20. A pair of trench depth regulating members 25 in the form of gauge wheels 24 may be respectively associated with the pair of discs of the double disc trench opener 20. More particularly, each gauge wheel 24 may be positioned generally in line with and immediately adjacent to the outside of each respective disc of the double disc trench opener 20. The gauge wheels 24 may be vertically adjusted to change the depth of the trench that is cut into the soil 27 using the double disc trench opener 20. A seed meter 32 may also be carried by frame 16. The seed meter 32 receives seed from a seed hopper 28 carried above the seed meter on the frame 16. The seed meter 32 delivers seed sequentially to a seed tube 36 through which the seed falls into or is otherwise placed into the trench 26.

A trench closer assembly 40 follows behind the gauge wheels 24 to close the trench 26 after the seed tube 36 places the seed within the trench 26. In various embodiments, the trench closer assembly 40 includes a soil contacting member 41 positioned generally in line with double disc trench opener 20 to push the soil 27 back into the trench 26 on top of the seeds deposited in the trench 26. The soil contacting member 41 may be biased generally downward toward the soil to exert a force on the soil 27. In one embodiment, the soil contacting member 41 are closing wheels 42. The closing wheels 42 may be made of metal or rubber and have a rounded or shaped peripheral edge (e.g., with teeth or tines), which may vary depending upon the application, and which are typically angled inward toward each other to push the soil 27 back into the trench 26 as they pass. In other embodiments, the soil contacting member 41 includes a packer wheel that follows the closing wheels to gently pack the soil surface. In yet other embodiments, the soil contacting member 41 is a drag closing system that may include a single wheel to push the seed into the trench followed by two or more drags that feather or rake loose soil over top of the seed within the trench 26. Other options are possible for the soil contacting member 41 and the trench closer assembly 40, in general.

In various embodiments, the trench closer assembly 40 can vary a force applied to the soil 27 by the soil contacting member 41. For example, the trench closer assembly 40 may include a variable biasing member 60 configured to bias the soil contacting member 41 toward the soil. In one example, a user can manually adjust the downforce of the variable biasing member 60, for example, by adjusting a setting of (e.g., a force exerted by) a biasing spring. In another example, the variable biasing member is an actuator 61 (e.g., an electrohydraulic cylinder, a pneumatic cylinder, or a linear actuator) or other device capable of changing the amount of downward force exerted by the soil contacting member 41 on the soil 27. Such a trench closer assembly 40 may be similar to that as disclosed in U.S. Pat. No. 8,910,582, titled "Row unit for a seeding machine having active downforce control for the closing wheels," the contents of which is incorporated herein by reference. The actuator 61 (or another device directly controlling the actuator 61) may be electrically controlled by a controller 70 (see FIGS. 3A and 3B) or may otherwise respond to signals from the controller 70, such that the controller 70 can control or dictate the amount of downward force applied by the soil 27 by the soil contacting member 41 by changing the operating parameters of the actuator 61. For example, if the actuator 61 is a pneumatic cylinder, the controller 70 can control the pressure within the pneumatic cylinder (or simply cause the pressure to increase or decrease), thereby controlling the downward pressure exerted by the soil contacting member 41 on the soil 27 (e.g., as the pressure increases, so does the downward force). Such control of the actuator 61, and its resulting downward force on the soil contacting member 41, may be automatically implemented by the controller 70 in one approach, or may be manually controlled by a user via a setting input on a user interface 76 (see FIGS. 3A and 3B) in another approach.

In certain approaches, the row planting unit 12 of the agricultural seeding machine 10 may also include a secondary closer member 90 that is configured to trail behind the trench closer assembly 40 to, when engaged, provide a second closing action on the trench 26. In one example, the secondary closer member 90 includes drag chains 92. However, in other examples, the secondary closer member 90 may include metal drags, an additional closing or firming wheel, additional smooth, serrated, or tined wheel or disc, or a wide packer wheel to name a few, which may vary on differing soil types and conditions. For example, as is shown in FIG. 4, instead of a drag chain 92, the secondary closer member 90 is shown as including a serrated closing wheel 97. As mentioned above, other types of secondary closer members are possible as well.

In certain approaches, the secondary closer member 90 may be engaged manually by a user, for example, by placing the secondary closer member 90 into an engaged position. However, in other embodiments, as with the trench closer assembly 40 discussed above, the secondary closer member 90 may also include a secondary actuator 94 to selectively engage and disengage the secondary closer member 90 with the soil 27. The secondary actuator 94 may include a linear actuator, a servomotor, an electrohydraulic cylinder, or a cable. The secondary actuator 94 (or another device directly controlling the secondary actuator 94) may be electrically controlled by the controller 70 (see FIGS. 3A and 3B) or may otherwise respond to signals from the controller 70, such that the controller 70 can control the engagement or disengagement of the secondary closer member 90. Such control of the secondary actuator 94, and its resulting engagement of the secondary closer member 90, may be automatically implemented by the controller 70 in one approach, or may be manually controlled by a user via a setting input on the user interface 76 (see FIGS. 3A and 3B) in another approach. In certain approaches, the secondary closer member 90 can be activated without adjusting the downward force applied by the trench closer assembly 40.

The row planting unit 12 of the agricultural seeding machine 10 also includes a sensing device 50. In various embodiments, the sensing device 50 is attached to the frame 16 or another portion of the row planting unit 12 and is arranged such that the sensing device 50 is oriented downward to detect the soil 27. In one approach, the sensing device is oriented and positioned behind the trench closer assembly 40 or the soil contacting member 41 to detect the soil 27 at a location where the trench closer assembly 40, or at least after the soil contacting member 41, has already passed and closed the trench 26 or a portion of the trench 26.

The sensing device 50 senses at least one aspect of the soil 27 within and surrounding a trench 26 without contacting the soil 27. In this manner, the sensing device advantageously does not disturb the soil 27 once the trench is covered. In one embodiment, the sensing device 50 senses a physical arrangement of the soil within and surrounding the trench 26. The sensing device 50 may comprise a radar system (e.g., a ground penetrating radar system) including a radar transmitter 78 and a radar receiver 80 (see FIGS. 3A and 3B). As is shown in FIGS. 3A and 3B, the radar transmitter 78 transmits electromagnetic radar signals downward toward the soil 27 and the radar receiver 80 receives reflected radar signals from the soil 27. One advantage of using a radar system as the sensing device 50 is that a radar system can detect aspects of the soil 27, such as its density and/or its physical arrangement, even in the presence of debris covering the trench 26 (e.g., plant debris). Further, a radar system can detect not only the top surface of the soil of the covered trench 26, but also the bottom of the trench 26. As the trench 26 is carved out of existing soil that may have been compacted down over time, the soil of the walls of the trench 26 are denser than the newly tilled loose soil used to cover up the trench 26. The radar system can detect a location or depth where the denser soil at the bottom of the trench 26 meets the looser tilled soil used to cover up the trench 26.

In other embodiments, the sensing device 50 may include other sensing or detecting systems that do not make physical contact with the soil 27, thereby not disturbing the soil 27. For example, the sensing device 50 may include a LIDAR (light radar) system, a time-of-flight camera system, or a stereo camera system to detect at least the top surface of the soil 27. Such systems may detect and analyze the top surface of the soil 27 to check for a height of the soil covering the trench, or to recognize openings or air pockets in the soil 27 covering the trench 26. These systems, in addition to the radar system discussed above, use or rely on electromagnetic waves, ultrasonic waves, or light, and thereby do not physically touch the soil 27 or disturb the soil 27 in any way.

In some embodiments, one or more row planting units 12 of the agricultural seeding machine 10, the agricultural seeding machine 10, or a tractor (not shown) may include a location sensor 51. Examples of such location sensors 51 include satellite navigation receiver, a Global Positioning System (GPS) receiver, a Differential GPS (DGPS) receiver, or a radio frequency telemetry receiver, to name a few). The location sensor 51 may be used to detect a current location of the agricultural seeding machine 10 or one or more row planting units 12 during operation; hence, to track or estimate the location (e.g., two or three-dimensional coordinates) of seeds planted in one or more rows, alone, or together with corresponding a trench closure data (e.g., trench closure quality indicator).

Figure 2:
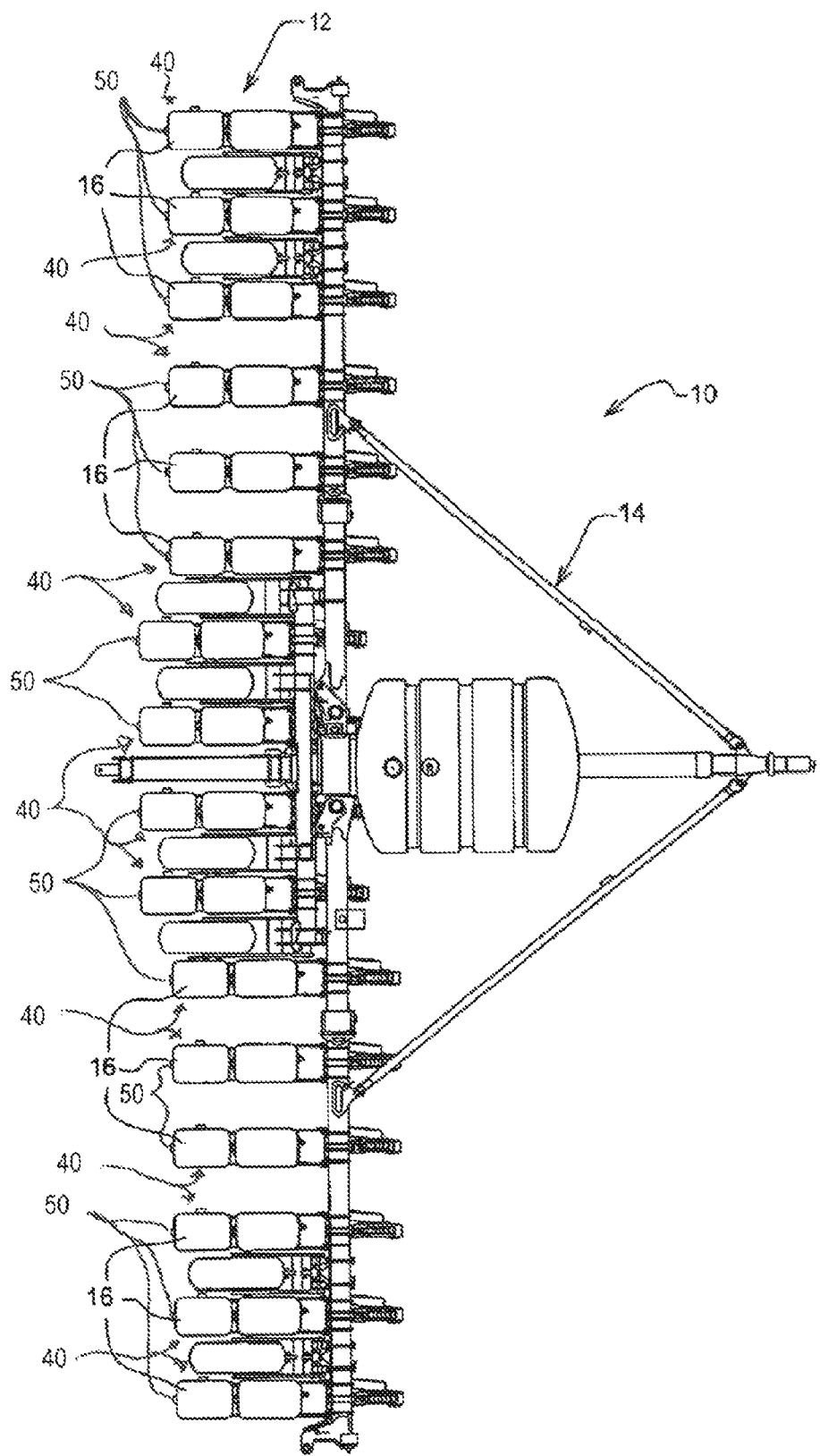
FIG. 2 shows a plurality of planting row units of an agricultural seeding machine according to various embodiments.

FIG. 2 shows an agricultural seeding machine 10 including a plurality of row planting units 12 according to various embodiments. In one example, each of the plurality of row planting units 12 includes a sensing device 50 and a trench closer assembly 40 comprising a soil contacting member 41 and a variable biasing member 60 (e.g., actuator 61). In this approach, the processing device 72 adjusts the variable biasing member 60 of each of the trench closer assemblies 40 in each row planting unit 12 to vary the force applied to the soil 27 by each soil contacting member 41 in each of the plurality of planter rows individually. That is, each soil contacting member 41 can be controlled independently according to the signals from the sensing device 50 associated with each individual row planting unit 12. Accordingly, optimal trench closing can be achieved for each individual row, thereby improving seed to soil contact and managing seed depth for each individual row to improve yield.

FIG. 3A shows an example schematic diagram of a portion of the agricultural seeding machine 10 according to various embodiments. Similar to FIG. 1, FIG. 3A also shows the sensing device 50 and the trench closer assembly 40 including a soil contacting member 41 and a variable biasing member 60, shown in FIG. 3A as an actuator 61. The trench closer assembly 40 pushes soil 27 over the trench 26 to cover the seeds placed in the trench 26.

The seeding machine 10 also includes a controller 70. The controller 70 may include one or more processing devices 72 coupled to one or more memories 74, for example, with a data bus 73. The processing device 72 may be a Central Processing Unit (CPU), microcontroller, or a microprocessor, and/or may include or be implemented with an Application Specific Integrated Circuit (ASIC), Programmable Logic Device (PLD), or Field Programmable Gate Array (FPGA); or as circuitry that includes discrete logic or other circuit components, including analog circuit components, digital circuit components or both; or any combination thereof. The circuitry may include discrete interconnected hardware components or may be combined on a single integrated circuit die, distributed among multiple integrated circuit dies, or implemented in a Multiple Chip Module (MCM) of multiple integrated circuit dies in a common package, as examples. The memory 74 may comprise a flash memory, a Random Access Memory (RAM), a Read Only Memory (ROM), an Erasable Programmable Read Only Memory (EPROM), a Hard Disk Drive (HDD), other magnetic or optical disk, or another machine-readable nonvolatile medium or other tangible storage mediums other than a transitory signal. The memory 74 may store therein software modules and instructions that, when executed by the processing device 72, cause the processing device 72 to implement any of the processes described herein or illustrated in the drawings. The memory 74 may also store other data for use by the processing device 72 such as, for example, reference signal characteristics, discussed below.

The seeding machine 10 may optionally include a user interface 76, for example, to provide real-time or historical information to a driver about the operation of the sensing device 50, the trench closer assembly 40, the secondary closer member 90, and the overall quality of closing of the trench. The user interface 76 may include a display screen that provides various textual and graphical data representing various information and data relating to the operation or settings of the row planting units 12 and/or the tractor. The user interface 76 may also comprise audible or sensory outputs that provide the user with audible (e.g., sounds or spoken words) or tactile information (such as seat rumbles or other vibrations). The user interface 76 may also include an input device for receiving commands from the user, such as a touch screen, buttons or switches, voice command, or the like. For example, the user interface 76 may provide the user with information about the status of the trenches after being closed such as an indication of a metric representative of a quality of trench closing by the trench closer assembly 40. The metric can represent trench closing across all of the row planting units 12, or the metric may represent the quality of trench closing for individual row planting units 12. The user interface 76 may also provide the user with other information about the soil, such as its density or a sensed depth of a moisture line. The user interface 76 may also provide the user with historical information or data structures of trench quality indicators versus corresponding location in a field, such as various statistics regarding the closure of the trenches, trench closure quality indicator associated with location information, and locations of areas within a field that might require additional work or reworking (e.g., map of trench closure quality that visually represents areas where the system met a set quality metric on trench closure quality or failed to close the trenches to a set quality metric on trench closure quality). The user interface 76 may also be capable of receiving inputs from the user. For example, the user interface 76 may provide the user with the ability to manually set or adjust the downward force applied by the trench closer assembly 40 (possibly within set upper and lower limits) and to manually engage or disengage the secondary closer member 90 via inputs. The user interface 76 can be located within a cab of a tractor to allow the user to receive information and provide commands while operating the tractor.

In accordance with various approaches, the controller 70, and in some implementations, the processing device 72 of the controller 70, is electrically coupled to the sensing device 50. In one optional approach, an analog-to-digital converter 69 is included within the connection between the sensing device 50 and the controller 70 to convert analog sensed signals from the sensing device 50 into digital signals to be processed by the processor 72 of the controller. In other embodiments, the sensing device 50 may output a digital signal, or the controller 70 may include at its input an analog-to-digital converter. The controller 70 may also be electrically coupled to the variable biasing member 60 or actuator 61 of the trench closer assembly 40, the secondary actuator 94 of the secondary closer member 90, and/or the user interface 76. In one embodiment, the controller 70 is electrically connected to another controller module (not shown) of the trench closer assembly 40 and/or the secondary closer member 90 that receives command signals from the controller 70 and adjusts the variable biasing member 60 or actuator 61 of the trench closer assembly 40 and/or engages or disengages the secondary closer member 90 accordingly.

In operation, the sensing device 50 mounted to the seeding machine 10 senses at least one aspect of the soil 27, such as its physical arrangement, without contacting the soil 27. As shown in FIGS. 3A and 3B, the sensing device 50 may be positioned behind the trench closer assembly 40 within a planting row and may sense the aspect of the soil at a location where the trench closer assembly 40 has already closed the trench 26. In one example, the sensing device 50 is a radar system (such as a ground penetrating radar system) including a radar transmitter 78 that emits radar signals 79 downward toward the soil 27 below and a radar receiver 80 that receives reflected radar signals 81 that are reflected from the soil 27 (e.g., from different depths of the soil) back toward the radar receiver.

Other sensing devices are possible. For example, a LIDAR system could be used, including a light (e.g., laser) transmitter and a light receiver (e.g., a camera or other optical sensor). In such an implementation, the light transmitter outputs light generally downward toward the soil 27 and the light receiver receives the reflecting light signal. Based on the timing or other aspects of the received light, the system can determine the distance to and general physical arrangement of the soil 27. In another similar example, the sensing device 50 may be a time of flight camera system that outputs light pulses toward the soil 27 and receives reflected light with a camera also pointed toward the soil. The time of flight camera system can then generally determine a three-dimensional image of the soil 27 to determine the physical arrangement of the top surface of the soil 27. In yet another example, the sensing device 50 may be a stereo camera system utilizing at least a pair of cameras and image processing to determine a three-dimensional image of the soil 27 to determine the physical arrangement of at least the top surface of the soil 27.

The sensing device 50 outputs to the processing device 72 of the controller 70 a sensed signal corresponding to the sensed aspect of the soil 27. The processing device 72 then receives the sensed signals from the sensing device 50. In the example in FIGS. 3A and 3B, the sensed signals are radar readings of the soil 27. In certain examples, the sensed signals correspond to a physical arrangement of the soil 27. In certain embodiments, the receiver 80 optionally includes an envelope detector 82. The optional envelope detector 82 can detect and/or measure an observed peak of a reflected signal 81 from the ground that equals or exceeds a reference threshold value. Based on this envelope/peak detection, the envelope detector 82 can send data or information to the processor 72 of the controller 70 for further processing. Alternatively, the receiver 80 can send a recorded digital representation of the signal of the envelope or the entire signal to the processor 72 for further processing. Also, in certain embodiments, the memory 74 may include or store therein a quality evaluator (e.g., program or software instructions), which, when executed by the processor 72, may perform all or some of the various trench closure quality indicators or determinations discussed below and herein.

The processing device 72 may determine that the sensed signal does not correspond to a desired aspect of the soil 27. In one example, the processing device 72 may determine that the sensed signal does not correspond to a desired physical arrangement of the soil 27. In particular, the processing device 72 may determine that the sensed signal indicates that the trench 26 is open (not fully closed or covered up by soil 27) or is poorly closed. For example, the processing device 72 may determine that the trench has portions that are not covered by soil 27, or that air pockets are within the soil 27. If the trench 26 is not properly closed or air pockets are in the soil 27 within the trench 26, the seeds within the trench may not have proper seed-to-soil contact, thereby reducing the likelihood of germination or slowing the timing of the germination. The processing device 72 may determine a metric representative of the quality of the trench closing by trench closer assembly 40 and may cause the user interface 76 to display or otherwise output an indication of that metric. In certain embodiments, the processing device 72 may also take corrective actions, discussed below.

In one approach, the processing device 72 may process the received sensed signals to determine a height of the soil 27 over the trench 26. The sensing device 50, and in particular a radar system, can detect the top surface of the soil relatively easy as the density difference between soil and air is relatively large. The processing device 72 may be aware of the height of the sensing device 50 above the ground and may determine the height of the top surface of the soil 27 covering the trench 26 based on the sensed distance of the top surface of the soil from the sensing device 50.

Alternatively, the processing device 72 may use other reference points to determine the height of the sensing device 50 or the height of the top surface of the soil 27. For example, the processing device 72 may process the sensed signals to determine an average height of the top surface of the soil 27 around the trench 26 and compare that distance to the distance to the soil actually covering the trench 26. In another approach, the processing device 72 may also detect a location or depth of the trench 26 (e.g., the bottom of the trench 26) due to the change in density of the soil at that location. The processing device 72 may then compare the location or depth of the bottom of the trench 26 with a detected location or depth for the top of the soil 27 covering the trench 26. The processing device 72 may then determine that the differences in these heights or locations corresponds to the thickness of soil covering the trench 26 to determine whether the trench 26 is properly covered. Similarly, because the processing device 72 may know, or may be able to determine the height of the sensing device 50 above the soil 27, the processing device 72 can process the returned sense signals (e.g., received radar signals) to look for a strong or a weak return signal at a particular height. If the signal is weak at a target height corresponding to a desired top of a properly covered trench 26, the processing device 72 may determine that the soil 27 over the trench 26 does not correspond to a desired height of the soil 27, indicating that the trench is open or poorly closed. In certain approaches, the processing device 72 may then take corrective actions, discussed below.

In certain embodiments, the processing device 72 is configured to process the sensed signals from the sensing device 50 to generate a processed sensed signal. For example, the processing device 72 may perform an envelope function on the sensed signals (e.g., radar readings if the sensing device 50 is a radar system) to generate the processed sensed signal. Many different envelope functions may be implemented, such as a peak envelope function, upper and lower envelope functions, an analytic envelope function, an RMS envelope function, or a Hilbert transform envelope function, to name a few. In general, as is understood in the art, an envelope function of a rapidly varying signal is a smooth curve outlining its extremes in amplitude. Thus, while the raw sensed signals from the sensing device may rapidly vary across small distances, the envelope function transforms that data to be a curve representing the extremes in the amplitudes of the raw sensed signals.

The processing device 72 may then compare a characteristic of the processed sensed signal to a stored signal characteristic representative of at least one soil condition. For example, the stored signal characteristic representative of the soil condition may be representative of a desired physical arrangement of the soil, such as an arrangement where the trench is fully closed and covered by soil. The stored signal characteristic may also be representative of an undesired physical arrangement of the soil, such as where the trench is open or only partially covered or partially closed. For example, the stored signal characteristic may be a reference envelope characteristic corresponding to an open trench, a closed trench, or a partially closed trench. In such an approach, the processing device 72 may compare the processed sensed signal characteristic to the stored signal characteristic representative of a closed trench, an open trench, or a partially closed trench. In processing the sensed signals and performing the comparison with the stored signal characteristic, the processing device 72 may then determine that that the sensed signals from the sensing device 50 do not correspond to the desired physical arrangement of the soil 27. For example, based on the comparison, the processing device 72 may determine that the processed sensed signal indicates that the trench 26 is not fully closed. In certain approaches, the processing device 72 may then use this feedback information to take corrective action regarding the operation of the trench closer assembly 40 and/or the secondary closer member 90 as discussed below.

The stored signal characteristic may be stored within the memory 74 and recalled by the processing device 72 for comparison. The stored signal characteristic may be pre-generated and pre-stored in the memory 74. There may be a plurality of stored signal characteristics corresponding to preferred and non-preferred arrangements of the soil. Further, there may be a plurality of stored signal characteristics corresponding to different soil types, different trench closer assembly types (e.g., closing wheels 42 versus a drag system). In various embodiments, the stored signal characteristics may be generated over time using machine learning, possibly receiving feedback from developers, users, or other devices indicating when a trench is closed well or closed poorly. In some embodiments, the stored signal characteristics may be updated periodically by a manufacturer or other manager of such data. The updates may be provided, for example, via the user interface 76 or may be downloaded and updated automatically via a communication system.

FIG. 3B shows an alternative example schematic diagram of a portion of the agricultural seeding machine 10 according to various embodiments. FIG. 3B is identical to FIG. 3A, except that FIG. 3B also includes the location sensor 51 electrically coupled to the controller 70. As the seeding machine 10 plants the seeds within the field and captures the trench closure data, the controller may store the metric of trench closure quality and associate that quality metric with a particular location received from the location sensor 51 within the memory 74.

FIG. 5 shows example graphs of sensed signals according to various embodiments. Graph 502 may represent an example graph of processed sensed signals. More particularly, graph 502 may represent the result of the processing device 72 performing an envelope function on the captured sensed signals from the sensing device 50. Similarly, in an alternative embodiment, graph 502 may represent the result of envelope detector 82 performing the envelope function on the captured sensed signals. Similarly, graph 506 may also represent another example graph of processed sensed signals also subject to the envelope function. In one example, these two graphs 502 and 506 may represent two different trench readings taken by the sensing device 50 at two different locations. The graph 502 may represent readings of a well-closed trench, while graph 506 may represent readings of a poorly closed or open trench. Graphs 504 and 508 represent the data of graphs 502 and 506, respectively, after optionally being processed by a filter, such as a low-pass filter or a smoothing filter, to smooth the envelope curves even further. This additional filtering step is not necessary, but may help with processing the signals in some approaches.

One indicator of a well-closed trench versus a poorly closed or open trench is a width of a peak envelope (e.g., an envelope that exists at a preset distance representing approximately the distance of the ground relative to the sensing device 50). For example, with radar systems, this first peak envelope may represent the highest reflected energy from reflections at the interface of air and soil at the surface of the soil 27. In various embodiments, a wider peak envelope, such as the peak envelopes 510 and 512 in graphs 502 and 504, respectively, represents a well-closed trench. Conversely, a narrower peak envelope, such as the peak envelopes 514 and 516 in graphs 506 and 508, respectively, represents a poorly closed or open trench. One way of determining peak envelope width may be to set a threshold 518 and measure the width of the distance from when where the upward curve of the peak envelope crosses the threshold 518 to where the downward curve of the envelope crosses the threshold 518 again. The processor 72 or the optional envelope detector 82 may perform this measurement. The width w1 is shown in graphs 502 and 504. Similarly, the width w2 is shown in graphs 506 and 508. The widths w1 may not be exactly the same in each graph 502 and 504, and the widths w2 may not be exactly the same in each graph 506 and 508, due to the filtering, but the respective widths may be approximately the same. As is shown, w1 is wider than w2, showing that the graphs 502 and 504 represent a closed trench, while the graphs 506 and 508 represent poorly closed or open trench. In one approach, the measured and determined peak envelope width can be compared against different set widths (as stored signal characteristics or stored reference envelope characteristics representative of different soil conditions) as to determine whether a trench is open, poorly closed, or well closed. For example, the quality evaluator 75, when executed by the processor 72, may perform these comparisons.

Alternatively, in one approach, the graphs 502 or 504 may represent a stored reference signal for a well closed trench, and/or the graphs 506 or 508 may represent a stored reference signal for a poorly closed or open trench. The processing device 72, executing the quality evaluator 75, may compare measured and processed sensed signals against these reference signals to determine whether the measured signal resembles the characteristics (e.g., envelope width, shape, etc.) of a reference signal to determine whether the sensed trench is closed, poorly closed, or open. Other variations are possible.

In various embodiments, the characteristic of the processed sensed signal may be a strength of the processed sensed signal at a preset height over the trench. Similarly, the stored signal characteristic representative of the soil condition may be an expected signal strength at the preset height over the trench, which corresponds to soil covering the trench at the perceived height. For example, the processing device 72 may be preprogrammed (e.g., according to the quality evaluator 75) to compare the processed signal strength (e.g., processed by an envelope function) at a certain preset depth down from the sensing device 50, which corresponds to the top of the soil of a properly closed trench, to an expected signal strength at the preset height over the trench corresponding to soil covering the trench at the preset height. If the trench is properly closed, then the signal at that depth, which is reflecting off of soil, will be stronger than an open or poorly closed trench, which may have a lower signal strength at that depth due to a lack of soil. In one example, the stored signal characteristic may a minimum signal strength, or a minimum relative signal strength relative to the signal strength for the perceived surrounding soil. The preset depth down from the sensing device 50 corresponds to a preset height over the trench. Alternatively, the processing device can continuously determine the depth of the surrounding soil and/or the bottom of the trench down from the sensing device 50 and can determine the depth down from the sensing device 50 that corresponds to the preset height over the trench. The preset height of the soil may be different based on different factors, such as soil type, crop being planted, planting technique, planting depth, trench closer assembly 40 utilized and other factors. Further, the processing device may change or adjust the preset height of the soil covering the trench based on machine learning techniques or in response to inputs received from a user.

In various embodiments, the processing device 72 (e.g., executing the quality evaluator 75) uses the sensed signals and/or the processed sensed signals as a feedback signal to determine how well the trench 26 is being closed. The quality evaluator 75 executed by the processing device 72 may determine a metric representative of the quality of the trench closing by trench closer assembly 40. For example, the metric may be a quantitative or qualitative measure of the quality of the trench closure, and may be based on the various methods discussed above for determining whether the trench 26 is closed. For example, the metric may be a tiered representation of various levels of trench closure quality (e.g., good, acceptable, borderline, poor, and open, etc.). Similarly, the metric may be a value representing percentage of the trench closed or open, which can be calculated according to different quantitative assessments included with any of the above discussed methods for determining whether the trench 26 is closed. Other metrics are possible, as well.

In some embodiments, the user interface 76 may display a map or some other visual indication of trench closure quality across various physical locations within a field. As mentioned above, as the seeding machine 10 plants the seeds within the field and captures the trench closure data, the controller may store the quality metric of trench closure and associate that quality metric with a particular location received from the location sensor 51 within the memory 74. Using this stored information, the user interface 76 may show a map that provides color-coded indications (or other visual indications) of trench closure quality on the map to associate the quality of the trench closure with a position within a field. The location information may also include trench number (e.g., corresponding to a particular row planter unit), planting pass number, and/or coordinates for different areas of interest. A user may be able to interact with the map, for example, to zoom in and out and to view more detailed information regarding various locations.

The processing device 72 may cause the user interface 76 to display or otherwise output an indication of the metric. For example, the user interface may provide a color representation for each different tier of trench closure quality (e.g., green meaning good, yellow meaning borderline, red meaning poor, etc.), and/or may provide a textual representation of that tier, or may provide a numeric quantity of the quality (e.g., a percentage closed). The user interface 76 may also provide an indication that too much downward force is applied to the trench by the trench closer assembly 40. The user interface 76 may also provide other information relating to the trench closure, such as a current downforce applied by the trench closer assembly 40 and a current engagement state of the secondary closer member 90. This information may be provided for individual row planting units 12 and/or for the entire planting system.

Based on all of this information provided via the user interface 76, if a user determines there is a need to adjust the force applied by the trench closer assembly 40 and/or engage/disengage the secondary closer member 90, in one approach, the user may halt the tractor and manually adjust the mechanical settings of the trench closer assembly 40 and/or the secondary closer member 90 within some or all row planting units 12. In another approach, where automated system are provided to vary the biasing force (e.g., via changing the variable biasing member 60 or actuator 61) of the trench closer assembly 40, or to engage/disengage the secondary closer member 90, the user interface 76 may receive commands from the user to vary such downward force or to selective engage/disengage the secondary closer member 90. Upon receipt of such commands, the processing device 72 may cause such changes to be implemented without the user having to stop the tractor and manually change the mechanical settings.

In certain approaches, if the processing device 72 determines the trench 26 is being closed poorly, the processing device 72 may take corrective action automatically. For example, the processing device 72 may compare the processed sensed signal characteristic to the stored signal characteristic representative of a soil condition, and may adjust the force applied to the soil 27 by the soil contacting member 41 of the trench closer assembly 40 in response to the comparison. For example, if the processing device 72 determines that the sensed signals do not correspond to a desired physical arrangement of the soil or indicate that the planting trench 26 is not fully closed (e.g., based on the comparison), the processing device 72 may responsively adjust or increase the force applied to the soil 27 by the soil contacting member 41 of the trench closer assembly 40. More specifically, the processing device 72 may adjust the variable biasing member 60 (e.g., an actuator 61) to vary a force applied to the soil 27 by the soil contacting member 41. By varying or increasing the force on the soil 27 by the soil contacting member 41, additional soil 27 may be moved from the side of the trench 26 toward the trench 26 to cover the trench 26 and the seeds therein.

Conversely, the processing device 72 may determine that the force applied to the soil 27 by the soil contacting member 41 is too high (e.g., by determining the height of the soil over the trench is too high, or that grooves on either side of the trench 26 formed by the soil contacting member 41 are too deep). The processing device 72 may then responsively vary or reduce the force applied to the soil 27 by the soil contacting member 41. If the force applied to the soil 27 by the soil contacting member 41 is too high, this may tend to cause seeds to be planted too deep, which can delay the timing of when the plants come up out of the ground. Further, too much downward force can slow down the speed of the planter by increasing draft forces or can increase fuel consumption.

In certain embodiments, the processing device 72 may determine to automatically engage the secondary closer member 90 to improve trench closure quality. For example, the processing device 72 may compare the processed sensed signal characteristic to the stored signal characteristic representative of a soil condition, and may engage or disengage the secondary closer member 90 in response to the comparison. For example, if the processing device 72 determines that the sensed signals do not correspond to a desired physical arrangement of the soil or indicate that the planting trench 26 is not fully closed (e.g., based on the comparison), the processing device 72 may responsively engage the secondary closer member 90. More specifically, the processing device 72 may operate the secondary actuator 94 to cause the secondary closer member 90 to engage the soil 27. The engagement/disengagement of the secondary closer member 90 may be determined independently of the downforce applied by the trench closer assembly 40 and/or with or without changing such downforce.

With reference briefly to FIG. 2, the system and methods discussed above can be utilized across a plurality of row planting units 12. For example, in various embodiments, the seeding machine 10 may include a plurality of sensing devices 50 corresponding to individual planting rows of the seeding machine 10. Alternatively, sensing devices 50 may sense more than one row of the seeding machine simultaneously. These multiple sensing devices 50 may sense the aspect of soil within and surrounding each planting trench of the plurality of planting rows without contacting the soil. The processing device 72 is coupled to the plurality of sensing devices 50 and receives sensed signals from the plurality of sensing devices 50. The processing device 72 also processes the plurality of sensed signal to generate a plurality of processed sensed signals and compares a characteristic of the plurality of processed sensed signals individually to the stored signal characteristic representative of the soil condition (e.g., signal strength at a preset height, or a determined height of the soil covering the trench). The multiple trench closer assemblies 40 proceed with closing the multiple planting trenches, and the processing device 72 adjusts the force applied to the soil by each of the soil contacting members 41 individually.

So configured, the processing device 72 continuously utilizes feedback information to determine how well the trench 26 is being closed. This feedback information can be used to provide an indication of the quality of the trench closer to a user via a user interface. Similarly, this feedback information can be used to continuously adapt the operation of the trench closer assembly 40 to provide optimal trench closing force. In this manner, the trench closure can be monitored and completed in manner that ensures proper seed-to-soil contact, helping the seeds to germinate properly and thereby reducing crop loss. Further, adjusting the trench closing in an optimal manner can help control the timing of when the plants in a field sprout, thereby providing a fairly uniform behavior of the crops and allowing for uniform treatment for the entire field during the growing season to optimize crop yield.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims. One skilled in the art will realize that a virtually unlimited number of variations to the above descriptions are possible, and that the examples and the accompanying figures are merely to illustrate one or more examples of implementations. It will be understood by those skilled in the art that various other modifications can be made, and equivalents can be substituted, without departing from claimed subject matter. Additionally, many modifications can be made to adapt a particular situation to the teachings of claimed subject matter without departing from the central concept described herein. Therefore, it is intended that claimed subject matter not be limited to the particular embodiments disclosed, but that such claimed subject matter can also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter can be practiced without these specific details. In other instances, methods, devices, or systems that would be known by one of ordinary skill have not been described in detail so as not to obscure claimed subject matter.

Various implementations have been specifically described. However, many other implementations are also possible.

What is claimed is:

1. An agricultural seeding machine comprising:
   a trench closer assembly comprising a soil contacting member, the trench closer assembly configured to vary a force applied to the soil by the soil contacting member;
   a sensing device configured to:
      sense at least one aspect of the soil without contacting the soil; and
      output a sensed signal corresponding to the at least one aspect of the soil;
   a processing device coupled to the sensing device, the processing device configured to:
      receive the sensed signal from the sensing device;
      process the sensed signal to generate a processed sensed signal at least in part by performing an envelope function on the sensed signal; and
      compare a width of a peak envelope of the processed sensed signal to at least one stored reference peak envelope width corresponding to at least one of an open trench or a closed trench to determine a metric representative of a quality of trench closing by the trench closer assembly;
   and a user interface coupled to the processing device and configured to output an indication of the metric.

2. The agricultural seeding machine of claim 1, wherein the processing device is further configured to:
   compare a strength of the processed sensed signal at a preset height over the trench against a stored expected signal strength at the preset height over the trench corresponding to soil covering the trench at the preset height.

3. The agricultural seeding machine of claim 1, wherein the processing device is coupled to the trench closer assembly, and wherein the processing device is further configured to:
   automatically adjust the force applied to the soil by the soil contacting member of the trench closer assembly responsive to the comparison.

4. The agricultural seeding machine of claim 3, wherein:
   the trench closer assembly further comprises at least one actuator configured to vary the force applied to the soil by the soil contacting member; and
   the processing device is configured to control the actuator to adjust the force applied to the soil by the soil contacting member of the trench closer assembly.

5. The agricultural seeding machine of claim 3, wherein the processing device is configured to:
   determine that the processed sensed signal indicates that the trench is not closed fully based, at least in part, on the comparison; and responsively increase the force applied to the soil by the soil contacting member of the trench closer assembly.

6. The agricultural seeding machine of claim 3, further comprising:
a plurality of planter rows, wherein each of the plurality of planter rows comprises a sensing device and a trench closer assembly comprising a soil contacting member; and
wherein the processing device adjusts the force applied to the soil by each soil contacting member in each of the plurality of planter rows individually.

7. The agricultural seeding machine of claim 1, wherein the sensing device is positioned behind the trench closer assembly within a planting row and is configured to sense the at least one aspect of the soil at a location where the trench closer assembly has already closed the trench.

8. The agricultural seeding machine of claim 1, wherein:
the sensing device comprises a radar system further comprising a radar transmitter and a radar receiver; and
the sensed signal comprises radar readings of the soil.

9. The agricultural seeding machine of claim 1, further comprising:
a secondary closer member configured to trail behind the trench closer assembly to provide a second closing action on the trench when engaged;
wherein the processing device is electrically coupled to the secondary closer member, and wherein the processing device is further configured to:
automatically engage the secondary closer member to contact the soil responsive to the comparison.

10. The agricultural seeding machine of claim 1, wherein the peak envelope exists at a preset distance from the sensing device representing approximately a distance of the ground relative to the sensing device.

11. The agricultural seeding machine of claim 1, wherein the processing device is further configured to determine the peak envelope as a portion of the processed sensed signal having a strength above a threshold strength value.

12. The agricultural seeding machine of claim 1, wherein the processing device is further configured to:
determine that the width of the peak envelope of the processed sensed signal is smaller than the at least one stored reference peak envelope width; and
responsively automatically increase the force applied to the soil by the soil contacting member of the trench closer assembly.

13. A method of closing a trench by a trench closer assembly of a seeding machine, the method comprising:
closing the trench with the trench closer assembly of the seeding machine, the trench closer assembly comprising a soil contacting member;
sensing, with a sensing device mounted to the seeding machine, at least one aspect of soil within and surrounding a planting trench without contacting the soil;
outputting, by the sensing device, a sensed signal corresponding to the at least one aspect of the soil;
receiving, by a processing device coupled to the sensing device, the sensed signal from the sensing device;
processing, by the processing device, the sensed signal to generate a processed sensed signal at least in part by performing an envelope function on the sensed signal;
comparing, by the processing device, a width of a peak envelope of the processed sensed signal to at least one stored reference peak envelope width corresponding to at least one of an open trench or a closed trench to determine a metric representative of a quality of trench closing by the trench closer assembly; and
outputting to a user interface coupled to the processing device, an indication of the metric.

14. The method of claim 13, wherein the sensed signal comprises radar readings of the soil; and
wherein the method further comprises comparing, by the processing device, a strength of the processed sensed signal at a preset height over the trench to an expected signal strength at the preset height over the trench corresponding to soil covering the trench at the preset height.

15. The method of claim 13, further comprising:
adjusting automatically, by the processing device, a force applied to the soil by the soil contacting member of the trench closer assembly responsive to the comparison.

16. The method of claim 13, further comprising:
automatically engaging, by the processing device, a secondary closer member to contact the soil responsive to the comparison, the secondary closer member configured to trail behind the trench closer assembly to provide a second closing action on the trench when engaged.

17. An agricultural seeding machine comprising:
a trench closer assembly comprising a soil contacting member and a variable biasing member configured to bias the soil contacting member toward soil;
a sensing device configured to:
after the trench closer assembly has closed a portion of a planting trench, sense a physical arrangement of the soil within and surrounding the portion of a planting trench using at least one of electromagnetic waves, ultrasonic waves, or light; and
output a sensed signal corresponding to the physical arrangement of the soil;
and a processing device coupled to the sensing device and the trench closer assembly, the processing device configured to:
receive the sensed signal from the sensing device;
process the sensed signal to generate a processed sensed signal at least in part by performing an envelope function on the sensed signal; and
compare a width of a peak envelope of the processed sensed signal to at least one stored reference peak envelope width corresponding to at least one of an open trench or a closed trench; and
adjust the variable biasing member to vary a force applied to the soil by the soil contacting member of the trench closer assembly responsive to the comparison.

18. The agricultural seeding machine of claim 17, further comprising:
a secondary closer member configured to trail behind the trench closer assembly to provide a second closing action on the trench when engaged;
wherein the processing device is electrically coupled to the secondary closer member, and wherein the processing device is further configured to:
automatically engage the secondary closer member to contact the soil responsive to the comparison.

19. The agricultural seeding machine of claim 17, wherein the sensing device comprises at least one of a ground penetrating radar system, a lidar system, a time-of-flight camera system, or a stereo camera system.

20. The agricultural seeding machine of claim 17, wherein the processing device is configured to:
determine that the width of the peak envelope of the processed sensed signal is smaller than the at least one stored reference peak envelope width and responsively determine that the sensed signal indicates that the planting trench is not fully closed; and responsively increase the force applied to the soil by the soil contacting member of the trench closer assembly.

* * * * *